(12) United States Patent
Arias et al.

(10) Patent No.: US 9,207,223 B2
(45) Date of Patent: Dec. 8, 2015

(54) CARTRIDGE BASED BREATH ALCOHOL CALIBRATION DEVICE

(71) Applicant: ALCO SYSTEMS SWEDEN AB, Järfälla (SE)

(72) Inventors: Miguel Arias, Hägersten (SE); Nigel Evans, South Glamorgan (GB)

(73) Assignee: Alco Systems Sweden AB, Järfälla (SE)

( * ) Notice: Subject to any disclaimer, the term of this patent is extended or adjusted under 35 U.S.C. 154(b) by 0 days.

(21) Appl. No.: 14/411,714

(22) PCT Filed: Jun. 27, 2013

(86) PCT No.: PCT/SE2013/050801
§ 371 (c)(1),
(2) Date: Dec. 29, 2014

(87) PCT Pub. No.: WO2014/003674
PCT Pub. Date: Jan. 3, 2014

(65) Prior Publication Data
US 2015/0177205 A1      Jun. 25, 2015

(30) Foreign Application Priority Data
Jun. 27, 2012   (SE) ..................... 1250707

(51) Int. Cl.
*G01N 33/98*      (2006.01)
*G01N 33/00*      (2006.01)
*G01N 33/497*     (2006.01)

(52) U.S. Cl.
CPC ........ *G01N 33/0006* (2013.01); *G01N 33/4972* (2013.01)

(58) Field of Classification Search
CPC ...................................................... G01N 33/98
USPC ........................................................ 73/1.03
See application file for complete search history.

(56) References Cited

U.S. PATENT DOCUMENTS 3,366,456 A * 1/1968 Andreatch et al. ............ 436/130
3,854,319 A * 12/1974 Burroughs et al. ............ 73/1.03
(Continued)

FOREIGN PATENT DOCUMENTS

CN      2444240Y  Y    8/2001
CN      201697906U U   1/2011
(Continued)

OTHER PUBLICATIONS

European Patent Office (ISA/EP), International Search Report of the ISA from PCT/SE2013/050801 completed Sep. 25, 2013 (total 4 pgs.).
(Continued)

*Primary Examiner* — Lisa Caputo
*Assistant Examiner* — Jamel Williams
(74) *Attorney, Agent, or Firm* — Barclay Damon, LLP

(57) ABSTRACT

A calibration device for a breath alcohol testing device includes a pump providing a controlled air flow at a predetermined rate, a chamber in fluid communication with the pump that receives the air flow from the pump, and an outlet opening in fluid communication with the chamber that allows the air flow to exit the chamber in which the chamber and/or outlet opening can be heated to a predetermined maintainable temperature during operation of the pump. The calibration device is releasably connected to or brought in fluid communication with a breath alcohol testing device such that the air flow exiting the outlet opening passes into the testing device. The calibration device receives a sealed cartridge containing a predetermined alcohol concentration in the chamber and further includes a lid for opening/closing the chamber wherein the cartridge can be pierced such that the air flow provided by the pump to the chamber will pass through the cartridge.

16 Claims, 1 Drawing Sheet

(56) References Cited

U.S. PATENT DOCUMENTS

| | | | |
|---|---|---|---|
| 6,096,558 A * | 8/2000 | Stock | 436/132 |
| 2008/0060409 A1 * | 3/2008 | Guth et al. | 73/1.03 |

FOREIGN PATENT DOCUMENTS

| | | |
|---|---|---|
| GB | 2029717 A | 3/1980 |
| JP | S58-196460 | 5/1985 |
| WO | WO9714947 A2 | 4/1997 |
| WO | WO2009111484 A2 | 9/2009 |
| WO | WO20120807187 A1 | 6/2012 |

OTHER PUBLICATIONS

European Patent Office (ISA/EP), Written Opinion of the ISA from PCT/SE2013/050801 completed Sep. 25, 2013 (total 5 pgs.).

Japanese Patent Office, Office Action (translation into English) in JP Patent Application No. JP 2015-518380, dated Aug. 4, 2015 (total 1 page).

State Intellectual Property Office (SIPO) China, Office Action (translation into English) in CN Patent Application No. Cn 20138003333.8, dated Jul. 21, 2015 (total 1 page).

* cited by examiner

CARTRIDGE BASED BREATH ALCOHOL CALIBRATION DEVICE

CROSS-REFERENCE TO RELATED APPLICATIONS

This application is a national stage application under 35 U.S.C. §371 of PCT/SE2013/050801 filed Jun. 27, 2013, which claims priority of SE 1250707-5, filed Jun. 27, 2012, each of these documents being hereby incorporated by reference in their entirety.

TECHNICAL FIELD

In a first aspect, the present invention relates to a calibration device for a breath alcohol testing device. In a second aspect, the present invention relates to a cartridge to be used in such a calibration device. In a third aspect, the present invention relates to a method of calibrating a breath alcohol testing device.

TECHNICAL BACKGROUND OF THE INVENTION

In recent times, equipment for testing breath alcohol concentration has become quite common even for personal use. There are a number of consumer or personal breath alcohol testers on the market. These hand-held devices are generally less expensive than the devices used by law enforcement.

Many handheld breath analyzers sold to consumers use a silicon oxide sensor (also called a semiconductor sensor) to determine the blood alcohol concentration. These sensors are prone to contamination and interference from substances other than breath alcohol and therefore require recalibration or replacement every six months. Higher end personal breath analyzers and professional-use breath alcohol testers commonly use platinum fuel cell sensors. These too require recalibration but at less frequent intervals than semiconductor devices, usually once a year.

Calibration is the process of checking and adjusting the internal settings of a breath analyser by comparing and adjusting its test results to a known alcohol concentration. Law enforcement breath analyzers are meticulously maintained and re-calibrated frequently to ensure accuracy.

There are two methods of calibrating a precision fuel cell breath analyzer, the wet bath and the dry gas method. Each method requires specialized equipment and factory trained technicians. It is not a procedure that can be conducted by untrained users or without the proper equipment.

The dry gas method utilizes a calibration standard which is a pre-certified solution containing a precise mixture of alcohol and inert nitrogen available in a pressurised container. The equipment may be portable allowing calibrations to be done when and where required.

The wet bath method utilizes an alcohol/water standard which is a pre-certified solution containing a precise specific alcohol concentration, contained and delivered in specialised breath alcohol simulator equipment. Wet bath apparatus has a higher initial cost than the dry gas method and is not intended to be portable. The standard must be fresh and replaced regularly.

These known methods often limit the end-user from calibrating and checking their own devices due to the high cost and complexity of obtaining certification themselves to produce the required equipment, or to purchase the required equipment from a certified supplier.

U.S. Pat. No. 3,854,319 discloses an alcoholic breath simulator wherein a sample may be simulated by blowing non-alcoholic breath through an elongated enclosure maintained at a given temperature and containing alcohol vapor continuously generated from an absorbent material impregnated with an alcohol-water solution. The breath produced at the enclosure's outlet will constitute a simulated breath sample having a known alcohol concentration. Drawbacks with this device are that the enclosure must be manually perforated and that it requires a non-alcoholic breath in order to give a correct calibration. Furthermore, the breath blown through the device might give rise to errors if not performed correctly, i.e. varying flow rate, insufficient volume etc.

WO 2009/111484 discloses calibration and accuracy check systems for a chemical sniffer, such as a breath alcohol tester, which utilize the dispensing of droplets with determinable concentration of alcohol and/or other liquids in a determinable number either directly to a reaction chamber, or into a carrier gas which can be sampled.

These known devices are still overly cumbersome and complex in use and do not achieve the desired simplicity and accuracy of calibration.

Therefore, there is a need to develop equipment which may be supplied to customers owning breath alcohol testing devices, such that they can perform calibration and testing using simple, inexpensive and disposable devices and methods.

SUMMARY OF THE INVENTION

The purpose of the present invention is to provide improved devices and methods for calibrating breath alcohol testing devices using simple, inexpensive and disposable equipment.

This is achieved by a calibration device, a cartridge to be used with the calibration device and a method for calibrating breath alcohol testing devices according to the claims.

According to one aspect of the present invention, there is provided a calibration device for a breath alcohol testing device. The calibration device comprises a pump configured to provide a controlled flow of air at a predetermined rate and a chamber in fluid communication with the pump and adapted to receive the flow of air from the pump, and an outlet opening in fluid communication with the chamber adapted to allow the flow of air to exit the chamber. Furthermore, the chamber comprises heating means configured to heat the chamber and/or outlet opening to a predetermined temperature and to maintain the predetermined temperature during operation of the pump. The calibration device is configured to be releasably connected to or brought in fluid communication with a breath alcohol testing device such that the flow of air exiting the outlet opening is passed into the breath alcohol testing device. The calibration device is adapted to receive a sealed cartridge containing a predetermined concentration of alcohol in the chamber and further comprises lid for opening/closing the chamber and co-operating with means for piercing the cartridge to pierce the cartridge upon closing of the lid such that the flow of air provided by the pump to the chamber will pass through the cartridge, thereby providing a sample containing the predetermined concentration of alcohol to the breath alcohol testing device.

Hence, the present invention solves the above problem by providing a calibration device which may be used together with inexpensive and disposable cartridges, which are manufactured and supplied under certification, in order to provide a one-shot sample of known alcohol concentration to calibrate/test a breath alcohol testing device.

Moreover, the user can easily and directly verify proper and correct insertion of the cartridge into the calibration device. In addition, the cartridge is held in place throughout the calibration process such that no air passing through the cartridge may escape from the chamber other than via the outlet opening. Handling of the cartridge for calibration is also simplified and secure, since the user does not need to manually pierce the seals.

In an alternative embodiment, the piercing means comprises a needle, a syringe and/or a knife. Thus, a clean and efficient piercing of the cartridge is achieved.

In a further preferred embodiment, the piercing means is configured to pierce the cartridge at opposite ends thereof, which allows for efficient flow of air through the cartridge ensuring that the ensuing sample exhibits a homogeneous alcohol concentration.

In an advantageous embodiment, the calibration device further comprises a controller for controlling operation of the pump and/or the heating means. This allows for efficient control of the pump and the heating means.

In another alternative embodiment, the calibration device further comprises means for indicating to a user that the predetermined temperature has been achieved in the chamber. Preferably, the indicating means comprises a light and/or a display. In this way, the user is provided with a clear indication that the calibration device is ready to be used for calibrating a breath alcohol testing device.

In a preferred embodiment, the calibration device further comprises input means allowing a user to select a volume of air to be provided by the pump and/or the predetermined temperature in the chamber. Thus, the user may choose the volume of air and/or the temperature of the sample provided by the calibration device in order to calibrate different breath alcohol testing devices requiring different input parameters for calibration or depending on ambient conditions (temperature, humidity, atmospheric pressure). Preferably, the predetermined temperature is set in the range 30-37° C., more preferably in the range 33-35° C. and most preferably the predetermined temperature is set to 34° C.

In an advantageous embodiment, the heating means comprises a thermistor to provide feedback for regulating the temperature.

In a second aspect of the present invention, there is provided a cartridge containing a predetermined concentration of alcohol and adapted to be used in the calibration device. The cartridge may be manufactured and supplied under certification to ensure accuracy of the calibration process.

In a preferred embodiment, the cartridge comprises a porous material with a pre-determined concentration of alcohol soaked therein. Preferably, the alcohol is ethanol, but any appropriate alcohol for calibrating a breath alcohol testing device may be used, as long as the concentration is known.

In an advantageous embodiment, the cartridge comprises a plastic tube enclosing the porous material and sealed at both ends thereof. Preferably, the seal comprises a foil material. The foil material may be any of metallic, plastic or combinations thereof to guarantee that the cartridge is protected from contamination until used in the calibration device according to the present invention. At the same time, the foil material should be readily pierceable to ensure proper functioning of the calibration device.

In a third aspect of the present invention, there is provided a method of calibrating a breath alcohol testing device. The method comprises the steps:

providing a calibration device configured to be releasably connected to or brought in fluid communication with a breath alcohol testing device;

wherein the calibration device comprises:

a pump configured to provide a controlled flow of air at a predetermined rate; and a chamber in fluid communication with the pump and adapted to receive the flow of air from the pump, and an outlet opening in fluid communication with the chamber adapted to allow the flow of air to exit the chamber;

heating the chamber and/or outlet opening to a predetermined temperature;

inserting a cartridge containing a predetermined concentration of alcohol into the chamber of the calibration device and piercing the cartridge such that the flow of air provided by the pump to the chamber will pass through the cartridge;

operating the pump to provide a flow of air through the cartridge whilst maintaining the predetermined temperature during operation of the pump;

passing the flow of air exiting the outlet opening, containing the predetermined concentration of alcohol, into the breath alcohol testing device.

By this method, simple and inexpensive calibration or testing of breath alcohol devices is achieved, thus allowing end-users to easily maintain the accuracy of their privately owned breath alcohol testing devices whilst eliminating high costs and/or long delays related to sending the equipment away to the supplier for re-calibration.

DETAILED DESCRIPTION OF THE INVENTION

Preferred embodiments of a calibration device and cartridge according to the present invention will now be described with reference to the attached drawings. The invention should not be considered to be limited to the embodiments shown in the attached drawings, but may be varied within the scope of the claims.

Figure 1:
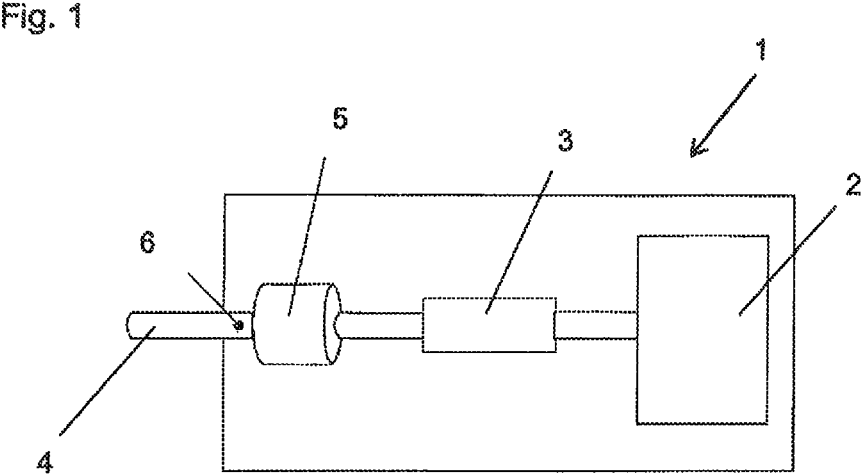
FIG. 1 illustrates a calibration device according to the present invention.

FIG. 1 shows a schematic illustration of a calibration device 1 according to the present invention. The calibration device 1 comprises a pump 2 to provide a controlled flow of air through the calibration device 1. Air is drawn from the ambient by the pump 2 and released at a predetermined rate. It is also possible to choose the desired flow rate by changing the settings for the pump 2.

A chamber 3 is provided in fluid communication with the pump 2 for receiving the flow of air provided by the pump 2. The calibration device 1 also comprises an outlet opening 4 in fluid communication with the chamber 3 adapted to allow the flow of air to exit the chamber 3.

The calibration device 1 also comprises heating means 5 configured to heat the chamber 3 and/or outlet opening 4 such that the flow of air provided by the pump 2 is given a temperature substantially equal to normal breath temperature, i.e. around 34° C. Of course, the calibration device 1 may also be set to heat the chamber 3 and/or outlet opening 4 to reach other temperatures, if desired. For example, the temperature of the flow of air may be set to a temperature in the range 30-40° C., or preferably 33-37° C., more preferably 34-36° C. This is to ensure that conditions for achieving an accurate and reliable calibration of breath alcohol testing devices are maintained.

The heating means 5 comprise a heating element 5 placed adjacent the outlet opening 4 to ensure that the flow of air exiting the chamber 3 reaches the desired predetermined temperature. Of course, the heating element may be placed anywhere in connection with the chamber 3, as long as the desired temperature of the flow of air exiting the chamber 3 is achieved. A thermistor 6 may be arranged adjacent the outlet opening 4 to provide feedback for regulating the temperature.

Access to the chamber 3 for inserting a calibration cartridge 7 is provided by means of a closable lid (not shown). The piercing means cooperates with the lid such that closing of the lid will cause the piercing means to pierce the cartridge 7. When the cartridge 7 is inserted and held in the chamber 3, actuation by means of a lever, button or slide switch in connection or co-operation with the lid will pierce the cartridge 7, thereby allowing the flow of air provided by the pump 2 to pass through the cartridge 7. The means for piercing the cartridge 7 may be a needle, a syringe, a knife or other means capable of cutting through the cartridge 7.

The calibration device 1 further comprises a (micro) controller (not shown) to control operation of the pump 2 and/or the heating means 5. The controller may be connected to indicating means for indicating to a user that the predetermined temperature has been reached in the form of a light signal or a display. Further, the controller is connected to input means allowing the user to select the desired predetermined temperature and/or the volume of air to be provided by the pump 2.

To ensure that no air escapes on its way from the calibration device 1 to the breath alcohol testing device, the outlet opening 4 is configured to be brought in fluid communication with the inlet tube of the breath alcohol testing device in a releaseable connection. One way of achieving a fluid tight connection is by providing corresponding threads on the outlet opening 4 and the inlet tube, one on the inside and one on the outside, respectively. Other fastening means may be considered, such as a snap or press-fit connection, a bayonet mount or similar.

Figure 2:
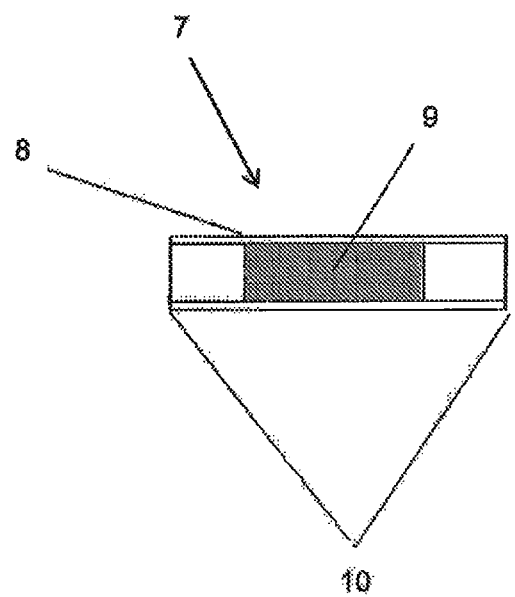
FIG. 2 illustrates a cartridge adapted to be used in a calibration device according to the present invention.

In FIG. 2, a cartridge 7 to be used with a calibration device 1 according to the present invention is shown. The cartridge 7 comprises a porous material 9 containing a predetermined concentration of alcohol which is used for calibrating a breath alcohol testing device. Preferably, the alcohol is ethanol, but any appropriate alcohol may also be used, as long as the concentration is known.

A plastic tube 8 encloses the porous material 9 and is sealed at both ends 10 to protect the porous material 9 and the predetermined alcohol concentration therein from contamination. Preferably, the seal comprises a foil or tinfoil material made of metal. Plastic or polymeric foils may also be considered.

In addition to protecting the contents of the cartridge 7, the seal also guarantees that the cartridge 7 has not been tampered with before being used for calibration.

Other shapes or forms of the cartridge 7 may also be considered such as discs, cans or canisters, capsules or pouches, as long as they are sealable and pierceable. In one embodiment, the cartridge 7 is sealed at opposing ends 10 and the piercing means is adapted to pierce both ends 10 of the cartridge 7, thus providing an efficient flow of air through the cartridge 7 to ensure that the air will carry with it the amount of alcohol contained in the cartridge 7.

In operation, the user wanting to calibrate his or her breath alcohol testing device first powers on the calibration device 1 which then starts to heat up to the predetermined temperature, e.g. 34° C. and connects it to the breath alcohol testing device. Once the calibration device 1 is ready, i.e. the predetermined temperature is reached, a signal is given to the user in the form of a light or an LCD message on the display.

The user then inserts a certified cartridge 7, containing a predetermined concentration of alcohol, into the chamber 3 of the calibration device 1 and closes the lid, thus piercing both ends 10 of the sealed plastic tube 8. After insertion of the cartridge 7, the user pushes a start button to operate the pump 2, which then starts pushing air through the cartridge 7, past the heating element and into the breath alcohol testing device. Thus a sample of predetermined concentration and volume is provided for easily and quickly calibrating the breath alcohol testing device is provided. After use, the cartridge 7 may be disposed of and a new cartridge 7 is inserted for each subsequent calibration.

The invention claimed is:

1. A calibration device for a breath alcohol testing device, wherein the calibration device comprises:
   a pump configured to provide a controlled flow of air at a predetermined rate;
   a chamber in fluid communication with the pump and adapted to receive the flow of air from the pump;
   an outlet opening in fluid communication with the chamber adapted to allow the flow of air to exit the chamber; and
   heating means configured to heat the chamber and/or outlet opening to a predetermined temperature and to maintain the predetermined temperature during operation of the pump,
   wherein the calibration device is configured to be releasably connected to or brought in fluid communication with a breath alcohol testing device such that the flow of air exiting the outlet opening is passed into the breath alcohol testing device,
   wherein the calibration device is adapted to receive a sealed cartridge containing a predetermined concentration of alcohol in the chamber and further comprises a lid for opening/closing the chamber and co-operating with means for piercing the sealed cartridge to pierce the cartridge upon closing of the lid such that the flow of air provided by the pump to the chamber will pass through the cartridge, thereby providing a sample containing the predetermined concentration of alcohol to the breath alcohol testing device.

2. The calibration device according to claim 1, wherein the piercing means comprises at least one of a needle, a syringe or a knife.

3. The calibration device according to claim 1, wherein the piercing means is configured to pierce the cartridge at opposite ends thereof.

4. The calibration device according to claim 1, further comprising a controller for controlling operation of at least one of the pump or the heating means.

5. The calibration device according to claim 1, further comprising means for indicating to a user that the predetermined temperature has been achieved.

6. The calibration device according to claim 5, wherein the indicating means comprises at least one of a light or a display.

7. The calibration device according to claim 1, further comprising input means allowing a user to select a volume of air to be provided by at least one of the pump or the predetermined temperature.

8. The calibration device according to claim 1, wherein the predetermined temperature is set in the range of 30-37° C.

9. The calibration device according to claim 8, wherein the predetermined temperature is set in the range of 33-35° C.

10. The calibration device according to claim 9, wherein the predetermined temperature is set to 34° C.

11. The calibration device according to claim 1, wherein the heating means comprises a thermistor.

12. The calibration device according to claim 1, wherein the cartridge contains a predetermined concentration of alcohol and is adapted to be used in the calibration device.

13. The calibration device according to claim 12, wherein the cartridge comprises a porous material with a pre-determined amount of alcohol soaked therein.

14. The calibration device according to claim 13, wherein the cartridge comprises a plastic tube enclosing the porous material and sealed at both ends thereof.

15. The calibration device according to claim 14, wherein the seal comprises a foil material.

16. A method of calibrating a breath alcohol testing device, comprising the steps of:
providing a calibration device configured to be releasably connected to or brought in fluid communication with a breath alcohol testing device;
wherein the calibration device comprises:
a pump configured to provide a controlled flow of air at a predetermined rate;
a chamber in fluid communication with the pump and adapted to receive the flow of air from the pump;
an outlet opening in fluid communication with the chamber adapted to allow the flow of air to exit the chamber; and
a lid for opening/closing the chamber and co-operating with means for piercing a sealed cartridge;
heating at least one of the chamber or outlet opening to a predetermined temperature;
inserting a sealed cartridge containing a predetermined concentration of alcohol into the chamber of the calibration device and piercing the sealed cartridge by closing the lid such that the flow of air provided by the pump to the chamber will pass through the cartridge;
operating the pump to provide a flow of air through the cartridge while maintaining the predetermined temperature during operation of the pump; and
passing the flow of air, containing the predetermined concentration of alcohol, exiting the outlet opening into the breath alcohol testing device.

* * * * *